United States Patent
Bornzin et al.

(10) Patent No.: US 6,490,489 B2
(45) Date of Patent: Dec. 3, 2002

(54) IMPLANTABLE CARDIAC SINGLE PASS CORONARY SINUS LEAD FOR PROVIDING PACING AND DEFIBRILLATION AND METHOD OF MANUFACTURE

(75) Inventors: Gene A. Bornzin, Simi Valley, CA (US); Anne M. Pianca, Valencia, CA (US); Kevin L. Morgan, Simi Valley, CA (US); John R. Helland, Saugus, CA (US); Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/771,505

(22) Filed: Jan. 26, 2001

(65) Prior Publication Data

US 2002/0103524 A1 Aug. 1, 2002

(51) Int. Cl.$^7$ .................................................. A61N 1/05
(52) U.S. Cl. .................................................... 607/122
(58) Field of Search ................................ 607/122, 123

(56) References Cited

U.S. PATENT DOCUMENTS

| | | | |
|---|---|---|---|
| 5,800,465 A | 9/1998 | Thompson et al. | 607/9 |
| 5,913,887 A * | 6/1999 | Michel | 607/123 |
| 5,964,795 A | 10/1999 | McVenes et al. | 607/122 |
| 6,001,085 A | 12/1999 | Lurie et al. | 604/282 |
| 6,070,101 A | 5/2000 | Struble et al. | 607/9 |

* cited by examiner

Primary Examiner—Scott M. Getzow

(57) ABSTRACT

A single chronic implantable cardiac lead for use in the coronary sinus region of the heart provides both atrial and ventricular pacing and defibrillation therapy. The lead includes an elongated lead body having a distal end and a proximal end, a first electrode assembly including a ventricular pacing electrode and a ventricular defibrillation at the distal end, a second electrode assembly proximal to the first electrode assembly including at least one atrial pacing electrode and an atrial defibrillation electrode, and a further defibrillation electrode proximal to the second electrode assembly. The electrode assemblies and further defibrillation electrode are spaced apart so that when the lead is implanted within the coronary sinus region of the heart with the first electrode assembly adjacent the left ventricle, the second electrode assembly is adjacent the left atrium and the further defibrillation electrode is within the right atrium and/or the superior vena cava.

7 Claims, 2 Drawing Sheets

IMPLANTABLE CARDIAC SINGLE PASS CORONARY SINUS LEAD FOR PROVIDING PACING AND DEFIBRILLATION AND METHOD OF MANUFACTURE

FIELD OF THE INVENTION

The present invention generally relates to an implantable cardiac lead for use with an implantable cardiac stimulation device. The present invention more particularly relates to such a lead adapted for use in the coronary sinus region of a heart and which includes all necessary electrodes for both defibrillation and pacing.

BACKGROUND OF THE INVENTION

Implantable cardiac stimulation devices are well known in the art. Such devices may include, for example, implantable cardiac pacemakers and defibrillators. The devices are generally implanted in a pectoral region of the chest beneath the skin of a patient within what is known as a subcutaneous pocket. The implantable devices generally function in association with one or more electrode carrying leads which are implanted within the heart. The electrodes are usually positioned within the right side of the heart, either within the right ventricle or right atrium, or both, for making electrical contact with their respective heart chamber. Conductors within the leads couple the electrodes to the device to enable the device to sense cardiac electrical activity and deliver the desired therapy.

Traditionally, therapy delivery had been limited to the venous, or right side of the heart. The reason for this is that implanted electrodes can cause blood clot formation in some patients. If a blood clot were released arterially from the heart left side, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, and cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

Cardiac leads intended for use in providing both cardiac pacing and defibrillation in the left heart via the coronary sinus region are difficult to position due to the tortuous venous routes of the human anatomy. Moreover, to provide both pacing and defibrillation of both the left atrium and the left ventricle from the coronary sinus region with multiple leads employing the appropriate types of electrodes is extremely difficult given the space constraints to accommodate multiple leads in the coronary sinus region. Hence, such implants are too cumbersome, difficult, and time consuming to perform and would likely result in compromised performance or system malfunction.

SUMMARY OF THE INVENTION

The present invention provides a single cardiac lead for implant in the cardiac sinus region of the heart. The lead includes all of the electrodes necessary for atrial pacing and defibrillation and ventricle pacing and defibrillation from the coronary sinus region. As a result, with the lead of the present invention, the implanter seeking such combined functionality need only implant a single lead.

In accordance with the present invention, the lead includes an elongated lead body having a distal end and a proximal end. A first electrode assembly including at least one pacing electrode and a defibrillation electrode is positioned at the distal end of the lead body. A second electrode assembly including at least one pacing electrode and a defibrillation electrode is positioned on the lead body proximal to the first electrode assembly. A further defibrillation electrode is positioned on the lead body proximal to the second electrode assembly. The first and second electrode assemblies and the further defibrillation electrode are spaced apart so that when the lead is implanted in the coronary sinus region of the heart with the first electrode assembly adjacent the left ventricle, the second electrode assembly is adjacent the left atrium and the further defibrillation electrode is within the right atrium and/or superior vena cava of the heart. The at least one pacing electrode of the first electrode assembly may be used to pace the left ventricle. The at least one pacing electrode of the second electrode assembly may be used for atrial pacing. The defibrillation electrode of the first electrode assembly together with the further defibrillation electrode may be used for ventricular defibrillation and the defibrillation electrode of the second electrode assembly together with the further defibrillation electrode may be used for atrial defibrillation.

The lead may further include a plurality of terminals and conductors for connecting the electrodes to an implantable cardiac stimulation device.

Further, the present invention provides a method of making the lead.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
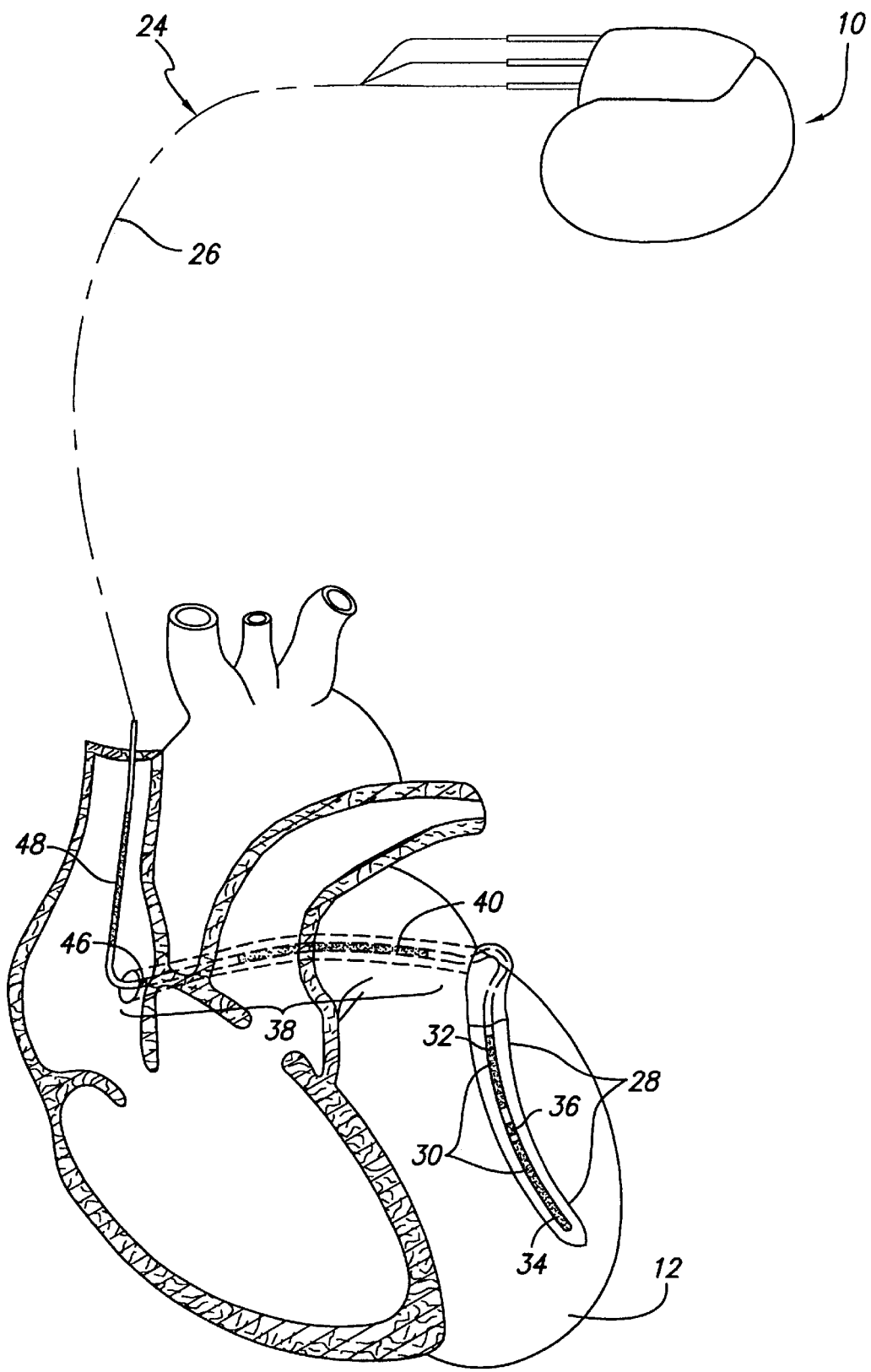
FIG. 1 is a simplified diagram illustrating an implantable cardiac stimulation device in electrical communication with a patient's heart by a coronary sinus region lead embodying the present invention.

As shown in FIG. 1, there is a stimulation device 10 in electrical communication with a patient's heart 12 by way of a coronary sinus region lead 24 embodying the present invention. Lead 24 provides both atrial pacing and defibrillation therapy and, in accordance with the present invention, left ventricular pacing and defibrillation therapy. The lead 24 is designed for placement in the "coronary sinus region" of the heart through the coronary sinus ostium and to extend adjacent to the left atrium and the left ventricle. As used herein, the phrase "coronary sinus region" refers to the venous vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

As will be noted in FIG. 1, the lead includes an elongated lead body 26 having a distal end which includes a first electrode assembly 28. Proximal to the first electrode assembly, the lead 24 also includes a second electrode assembly 38, and proximal to the electrode assembly 38, a right atrium (RA) and/or superior vena cava (SVC) defibrillation electrode 48. The first and second electrode assemblies and the RA/SVC defibrillation electrode are spaced apart on the lead body so that when the lead 24 is implanted in the coronary sinus region with the first electrode assembly 28 being adjacent the left ventricle, the second electrode assembly 38 is adjacent the left atrium and the RA/SVC electrode 48 is within the RA/SVC.

The electrode assembly 28 includes a defibrillation electrode 30 including a first portion 32 and a second portion 34. In between the first and second defibrillation electrode portions 32 and 34 is at least one pacing electrode 36. The defibrillation electrode portion 34 extends from a point distal to the pacing electrode 36 to the distal tip or adjacent to the distal tip end of the lead. In accordance with this embodiment, the defibrillation electrode is a coil electrode wherein the defibrillation electrode portions 32 and 34 are formed of electrical coils. The electrode portions 32 and 34 are coupled together and are electrically isolated from the pacing electrode 36.

The pacing electrode 36 supports both sensing of cardiac activity of the heart and the delivery of pacing stimulation pulses to the left ventricle. The defibrillation electrode 30 provides delivery of defibrillation stimulation pulses through the left ventricle because electrode 30 extends along the left ventricle. The defibrillation electrode 30 is preferably employed for defibrillation in conjunction with the right atrium/superior vena cava coil electrode 48. Also, since the at least one pacing electrode 36 is immediately adjacent the left ventricle, it will provide effective left ventricular pacing and sensing as well.

The second electrode assembly 38 includes an at least one atrial pacing electrode 46 and a left atrial defibrillation coil electrode 40. The at least one pacing electrode 46 may be spaced from the defibrillation electrode 40 so as to be positioned either in the right atrium to provide right atrial pacing and sensing or adjacent the left atrium to provide left atrial sensing and pacing. The defibrillation coil electrode 40 permits atrial defibrillation stimulation pulses to be delivered across both atria when used in conjunction with the RA/SVC electrode 48. Alternatively, the electrode assembly 38 may be configured in the same manner as electrode assembly 28. Further, the electrode assembly 28 may be configured in the same manner as electrode assembly 38.

Figure 2:
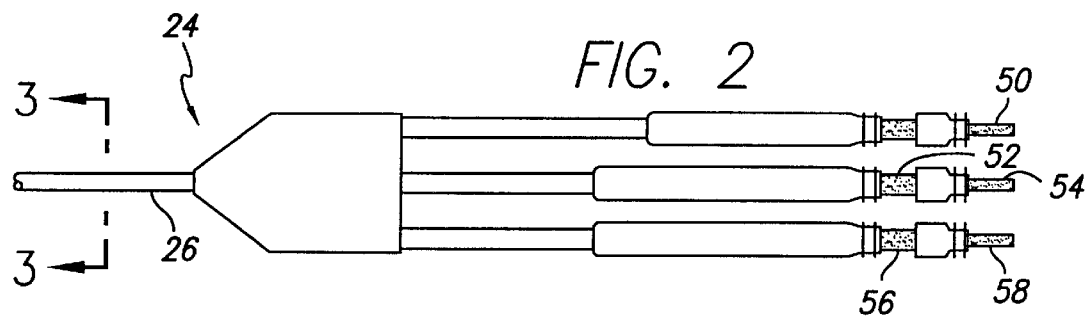
FIG. 2 is a side plan view, to an enlarged scale, of the proximal end of the lead of FIG. 1.
Figure 3:
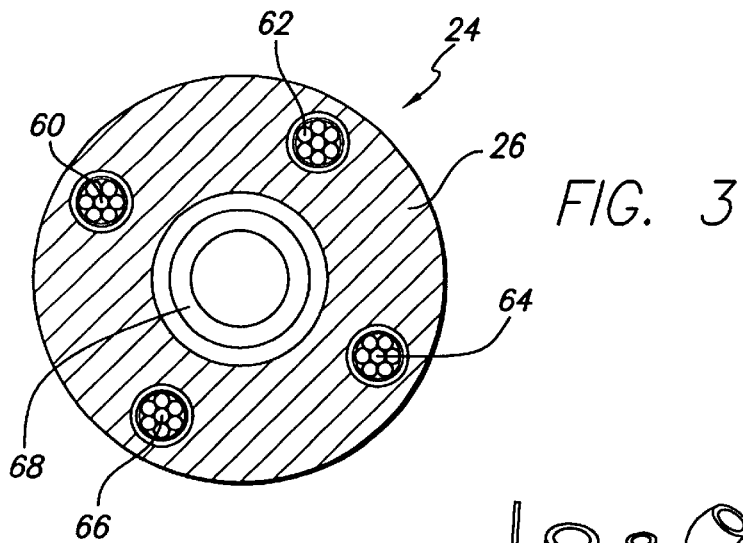
FIG. 3 is a cross-sectional view taken along lines 3—3 of FIG. 2.

FIGS. 2 and 3 show the proximal end of the lead 24 of FIG. 1. The elongated lead body 26 includes, at its proximal end, a plurality of terminals 50, 52, 54, 56, and 58. The lead body further includes a plurality of lumen conductors 60, 62, 64, and 66 which may be of coil or cable configuration and a conductor coil 68 into which a guiding stylet may be inserted for use during implant. The lumen conductors and coil conductor electrically connect each terminal to a respective different lead electrode. For example, terminal 50 may be connected to the RA/SVC defibrillation electrode 48 by conductor 60, terminal 52 may be connected to the left atrial defibrillation electrode 40 by conductor 62, terminal 54 may be connected to the atrial pacing electrode 46 by conductor 64, terminal 56 may be coupled to the left ventricular defibrillation electrode 30 by the conductor 66, and terminal 58 may be coupled to the left ventricular pacing electrode 36 by the stylet coil 68.

Figure 4:
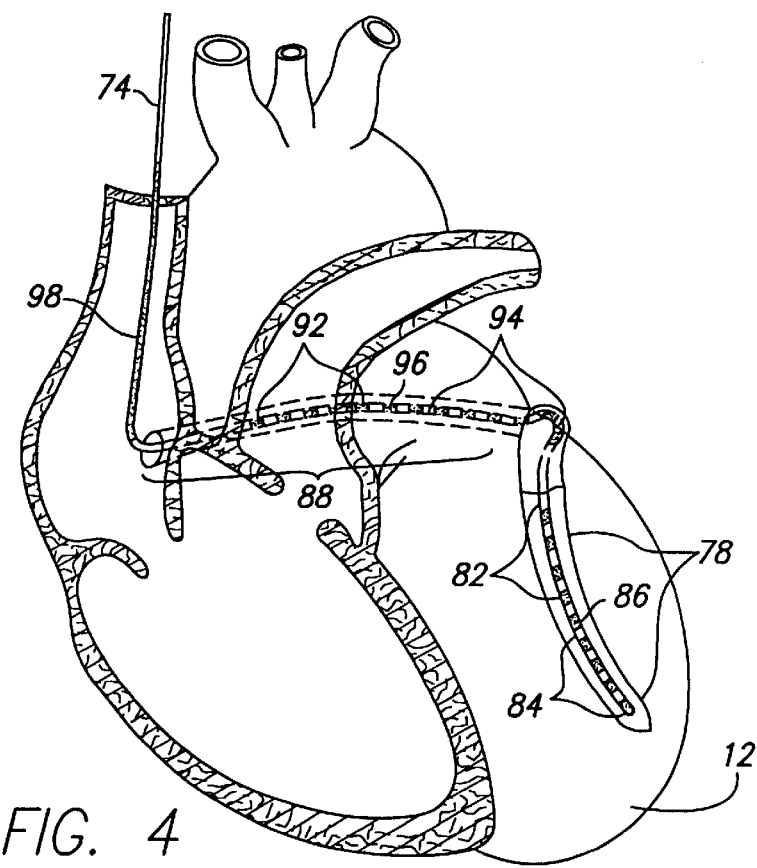
FIG. 4 is a simplified diagram of a human heart illustrating another coronary sinus region lead embodying the present invention.

FIG. 4 shows still another coronary sinus region lead 74 embodying the present invention. The lead 74, like lead 24 of FIG. 1 is configured to deliver atrial pacing stimulation pulses, sense atrial activity, deliver defibrillation stimulation pulses to the left and right atria, deliver pacing stimulation pulses to the left ventricle, sense ventricular activity, and deliver defibrillation stimulation pulses to the left ventricle. To provide such functionality, the lead 74 includes a left ventricular electrode assembly 78, a left atrial electrode assembly 88, and a RA/SVC defibrillation coil electrode 98. The ventricular electrode assembly 78 is positioned at the distal end of the lead 74 and includes a ventricular pacing electrode 86 and a ventricular defibrillation electrode comprising a first portion formed by a first group 82 of ring electrodes and a second portion formed by a second group 84 of ring electrodes. The ring electrodes of the defibrillation electrode are coupled together but electrically isolated from the pacing electrode 86. Again, the second portion or group of ring electrodes 84 extends from a point distal to the pacing electrode 86 to the distal tip or adjacent to the distal tip end of the lead 74.

Similarly, the atrial electrode assembly includes an atrial pacing electrode 96 and an atrial defibrillation electrode comprising a first portion formed by a first group 92 of ring electrodes and a second portion formed by a second group 94 of ring electrodes. Again, the defibrillation electrode ring electrodes are coupled together but electrically isolated from the pacing electrode 96.

As thus can be seen from the foregoing, the present invention provides a coronary sinus region implantable lead which provides both atrial and ventricular pacing and defibrillation therapy. The defibrillation electrodes and pacing electrodes are positioned to provide efficient pacing and defibrillation therapy from a single lead. This allows for the implanter to achieve complete stimulation therapy while only implanting a single lead in the coronary sinus region.

While the invention has been described by means of specific embodiments and applications thereof, it is understood that numerous modifications and variations could be made thereto by those skilled in the art without departing from the spirit and scope of the invention. It is therefore to be understood that within the scope of the claims the invention may be practiced otherwise than as specifically described herein.

What is claimed is:

1. A chronic implantable cardiac lead for use in the coronary sinus region of a heart, the lead comprising:
- an elongated lead body having a distal end and a proximal end;
- a plurality of terminals at the proximal end of the lead body;
- a first electrode assembly including a defibrillation electrode and at least one pacing electrode at the distal end of the lead body;
- a second electrode assembly proximal to the first electrode assembly, the second electrode assembly including a defibrillation electrode and art least one pacing electrode;
- a further defibrillation electrode proximal to the second electrode assembly; and
- a plurality of conductors connecting each electrode to a respective given one of the terminals,
    - the electrode assemblies and the further defibrillation electrode being spaced apart so that when the lead is implanted in the coronary sinus region of the heart with the first electrode assembly adjacent the left ventricle of the heart, the second electrode assembly is adjacent the left atrium of the heart and the further defibrillation electrode is within the right atrium and/or superior vena cava of the heart;
    - wherein the defibrillation electrode of one of the first and second electrode assemblies includes a first electrode portion proximal its corresponding at least one pacing electrode and a second electrode portion distal to its corresponding pacing electrode.

2. The cardiac lead of claim 1 wherein the first and second electrode portions each comprise an electrical coil.

3. The cardiac lead of claim 1 wherein the first and second electrode portions comprise a first and second respective group of ring electrodes.

4. The cardiac lead of claim 1 wherein the defibrillation electrode of the first electrode assembly includes a first electrode portion proximal its corresponding at least one pacing electrode and a second electrode portion distal to its corresponding pacing electrode.

5. The cardiac lead of claim 4 wherein the first and second electrode portions each comprise an electrical coil.

6. The cardiac lead of claim 4 wherein the first and second electrode portions comprise a first and second respective group of ring electrodes.

7. The cardiac lead of claim 4 wherein the second electrode portion extends adjacent to, or to the distal end of the lead.

* * * * *